(12) United States Patent
Allio et al.

(10) Patent No.: US 12,383,513 B1
(45) Date of Patent: Aug. 12, 2025

(54) MEDICINAL COMPOSITION, METHOD OF MANUFACTURE, AND METHOD FOR TREATING SKIN AILMENTS SUCH AS PALMAR-PLANTAR ERYTHRODYSESTHESIA

(71) Applicant: St. James Therapeutics Inc., Akron, OH (US)

(72) Inventors: Laura Allio, Copley, OH (US); Michael Allio, Copley, OH (US)

(73) Assignee: St. James Therapeutics Inc., Akron, OH (US)

(*) Notice: Subject to any disclaimer, the term of this patent is extended or adjusted under 35 U.S.C. 154(b) by 228 days.

(21) Appl. No.: 17/932,690

(22) Filed: Sep. 16, 2022

Related U.S. Application Data (62) Division of application No. 16/523,444, filed on Jul. 26, 2019, now Pat. No. 11,471,427.

(60) Provisional application No. 62/711,149, filed on Jul. 27, 2018.

(51) Int. Cl.
| | |
|---|---|
| A61K 31/122 | (2006.01) |
| A61K 9/00 | (2006.01) |
| A61K 31/704 | (2006.01) |
| A61K 36/32 | (2006.01) |
| A61K 36/53 | (2006.01) |
| A61K 36/61 | (2006.01) |
| A61K 36/886 | (2006.01) |
| A61K 36/889 | (2006.01) |
| A61K 45/06 | (2006.01) |

(52) U.S. Cl.
CPC .......... *A61K 31/122* (2013.01); *A61K 9/0019* (2013.01); *A61K 31/704* (2013.01); *A61K 36/32* (2013.01); *A61K 36/53* (2013.01); *A61K 36/61* (2013.01); *A61K 36/886* (2013.01); *A61K 36/889* (2013.01); *A61K 45/06* (2013.01)

(58) Field of Classification Search
CPC ... A61K 31/122; A61K 31/704; A61K 9/0019
See application file for complete search history.

(56) References Cited

U.S. PATENT DOCUMENTS

| | | |
|---|---|---|
| 5,888,984 A | 3/1999 | Brown |
| 6,280,751 B1 | 8/2001 | Fletcher et al. |
| 7,691,419 B2 | 4/2010 | DiLeva |
| 8,623,335 B2 | 1/2014 | Waddington |
| 8,685,381 B2 | 4/2014 | Schlessinger et al. |

FOREIGN PATENT DOCUMENTS

| | | |
|---|---|---|
| CN | 105640809 | 6/2016 |

OTHER PUBLICATIONS

The Editors of Encyclopedia Britannica. Henna. In: Encyclopedia Britannica, Inc. https://www.britannica.com/plant/henna. Published May 24, 2018. Accessed Sep. 10, 2018.
U.S. Department of Health, Food and Drug Administration. Temporary Tattoos, Henna/Mendhi, and "Black Henna": Fact Sheet. https://www.fda.gov/cosmetics/productsingredients/products/ucm108569..htm. Updated Jul. 25, 2017. Accessed Sep. 10, 2018.
Cartwright-Jones C. The Henna Page. http://www.hennapage.com/henna/. Accessed Sep. 10, 2018.
Petkewich R. Henna. Chem Eng News. 2006; 84(6): 28. https://pubs.acs.org/cen/whatstuff/84/8406 henna.html.
SCCS (Scientific Committee on Consumer Safety), Opinion on Lawsonia inermis (henna). Published Sep. 19, 2013. Accessed Sep. 10, 2018. https://ec.europa.eu/health/scientific_committees(consumer_safety/docs/sccs_o_140.pdf.
Alia BH, Bashir AK, Tanira MOM. Anti-inflammatory, antipyretic, and analgesic effects of Lawsonia inermis L. (henna) in rats. Pharmacology 1995;51(6):356-363. https://www.karger.com/Article/Abstract/139347.
Chaudhary G, Goyal S, Poonia P. Lawsonia inermis Linnaeus: A Phytopharmacological Review. Int J of Pharm Sci Drug Res 2010; 2(2): 91-98. http://ijpsdr.com/ContentPaper/2010-2-2-2.pdf.
Agarwal P, Alok S, Verma A: An update on Ayurvedic herb henna (*Lawsonia inermis* L.): a review. Int I Pharm Sci Res 2014; 5(2): 330-39.
Yucel I, Guzin G. Topical henna for capecitabine induced hand-foot syndrome. Invest New Drugs. 2008;26(2):189-192.
Ilyas S, Wasif K, Saif MW. Topical henna ameliorated capecitabine-induced hand-foot syndrome. Cutan Ocul Toxicol. 2014;33(3):253-255.
Kraeling ME, Bronaugh RL, Jung CT. Absorption of lawsone through human skin. Cutan Ocul Toxicol. 2007;26(1):45-56.
SCCPNFP (Scientific Committee on Cosmetic Products And Non-Food Products Intended For Consumers), Opinion on Lawsone. Published Feb. 16, 2004. Accessed Sep. 10, 2018. http://ec.europa.eu/health/ph_risk/committees/sccp/documents/out254_en.pdf.
EU Commission (2005). Draft Commission Directive . . . / . . . /EC of amending Council Directive 76/768/EEC, concerning cosmetic products, for the purposes of adapting Annexes II and III thereto to technical progress (regarding Lawsone and Lawsonia inermis).

(Continued)

*Primary Examiner* — Kevin E Weddington
(74) *Attorney, Agent, or Firm* — Emerson, Thomson & Bennett, LLC; Roger D. Emerson; Peter R. Detorre (57) ABSTRACT

The present disclosure relates to a medicinal composition and related methods using Lawsone (2-hydroxy-1,4-naphthoquinone) as a key active ingredient for treating pain associated with chemotherapy-induced palmar plantar erythrodysesthesia (Hand-Foot Syndrome). The medicinal composition may be administered topically as a gel, ointment, cream, lotion, suspension, spray, transdermal patch or liquid alone or in combination with other topical steroids, topical NSAIDS, antiarrhythmics, moisturizers, capsaicin, emollients, herbal remedies and essential or carrier oils. The medicinal composition eliminates the pain and burning sensation experienced with palmar-plantar erythrodysesthesia and allows patients to carry on with normal daily activities after a session of chemotherapy.

11 Claims, 7 Drawing Sheets

(56) References Cited

OTHER PUBLICATIONS

VKM (Norwegian Scientific Committee for Food Safety). Opinion of the Panel on Food Additives, Flavourings, Processing Aids, Materials in Contact with Food, and Cosmetics of the Norwegian Scientific Committee for Food Safety: Comments concerning Henna (*Lawsonia inermis*) for hair-dyeing. Published Jul. 1, 2005. Accessed Sep. 10, 2018. https://vkm.no/download/-18.645b840415d03a2fe8f1402b/1500910874435/d63ccd25cf.pdf.

Ali BH, Bashir AK, Tanira MO. Anti-inflammatory, antipyretic, and analgesic effects of *Lawsonia inermis* L. (henna) in rats. Pharmacology. 1995;51(6):356-363.

U.S. Department of Health, Food and Drug Administration. Is It a Cosmetic, a Drug, or Both? (Or Is It Soap?). http://www.fda.gov/cosmetics/guidanceregulation/lawsregulations/ucm074201.htm. Published Apr. 30, 2012. Accessed Sep. 10, 2018.

U.S. Department of Health, Food and Drug Administration. Wrinkle Treatments and Other Anti-aging Products. https://www.fda.gov/cosmetics/productsingredients/products/ucm388826.htm. Published Feb. 28, 2018. Accessed Sep. 10, 2018.

U.S. Department of Health, Food and Drug Administration. Guidance for Industry: Cosmetic Good Manufacturing Practices.https://www.fda.gov/downloads/Cosmetics/GuidanceRegulation/GuidanceDocuments/UCM358287.pdf. Updated Jun. 2013. Accessed Sep. 10, 2018.

U.S. Department of Health, Food and Drug Administration. Good Manufacturing Practice (GMP) Guidelines/Inspection Checklist. https://www.fda.gov/cosmetics/guidanceregulation/guidancedocuments/ucm2005190.htm. Updated Apr. 24, 2008. Accessed Sep. 10, 2018.

U.S. Department of Health, Food and Drug Administration. Cosmetic Labeling Guide. https://www.fda.gov/cosmetics/labeling/regulations/ucm126444.htm. Updated Nov. 25, 2017. Accessed Sep. 10, 2018.

Federal Trade Commission. Fair Packaging and Labeling Act. https://www.ftc.gov/enforcement/rules/rulemaking-regulatory-reform-proceedings/fair-packaging-labeling-act. Updated Feb. 16, 2018. Accessed Sep. 10, 2018.

Electronic Code of Federal Regulations. Listing of Color Additives Exempt from Regulation. §73.2190. Henna. https://www.ecfr.gov/cgi-bin/retrieveECFR?gp=&SID=17723345ba7c363ef25a68e9776aa2cd&r=PART&n=21y1.0.1.1.27#se21.1.73_12190.

U.S. Department of Health, Food and Drug Administration. Guidance for Industry: Lead in Cosmetic Lip Products and Externally Applied Cosmetics: Recommended Maximum Level. https://www.fda.gov/Cosmetics/GuidanceRegulation/GuidanceDocuments/ucm452623.htm. Published Dec. 2016. Accessed Sep. 10, 2018.

U.S. Department of Health, Food and Drug Administration. Small Businesses and Homemade Cosmetics: Fact Sheet. https://www.fda.gov/cosmetics/resourcesforyou/industry/ucm388736.htm#3. Updated Sep. 4, 2018. Accessed Sep. 10, 2018.

U.S. Department of Health, Food and Drug Administration. Prohibited and Restricted Ingredients. https://www.fda.gov/Cosmetics/GuidanceRegulation/LawsRegulations/ucm127406.htm. Updated Nov. 3, 2017. Accessed Sep. 10, 2018.

Scontre, Vanessa Armenio, et al. *Curcuma longa* (Turmeric) for Prevention of Capecitabine-Induced Hand-Foot Syndrome: A Pilot Study Crossref DOI link: https://doi.org/10.1080/19390211.2017.1366387 Published: Sep. 3, 2018, Journal of Dietary Supplements, vol. 15, 2018—Issue 5.

Kang, Yoon-Koo, et al. Pyridoxine Is Not Effective to Prevent Hand-Foot Syndrome Associated With Capecitabine Therapy: Results of a Randomized, Double-Blind, Placebo-Controlled Study; J. Clin. Onc. doi: 10.1200/JCO.2010.29.1807. Epub Jul. 12, 2010.

Zhang, Rong-Xin, et al. The Effect of COX-2 Inhibitor on Capecitabine-Induced Hand-Foot Syndrome in Patients With Stage II/III Colorectal Cancer: A Phase II Randomized Prospective Study; J Cancer Res Clin Oncol. Jun. 2011; 137(6):953-7. doi: 10.1007/s00432-010-0958-9. Epub Nov. 27, 2010.

Saif, Muhammad Wasif. Capecitabine and hand-foot syndrome; Expert Opinion on Drug Safety; vol. 10, 2011, Issue 2; https://doi.org/10.1517/14740338.2011.546342; pp. 159-169 | Published online: Dec. 22, 2010.

Keshavarz, Abdollah, et al. Efficacy of Traditional Medicine Product Henna and Hydrocortisone on Diaper Dermatitis in Infants; Iran Red Crescent Med. J. May 2016;18(5):e24809; Published online Feb. 22, 2016.

U.S. National Library of Medicine, Topical Henna Preparation for the Treatment of Hand Foot Skin Syndrome, First Posted Apr. 2, 2010, Last Update Posted Dec. 12, 2014.

Admin, "Henna: Bringing Relief to Cancer Patients", https://hennablogspot.com/henna-bringing-relief-to-cancer-treatments/, published Jan. 11, 2009.

"How to Mix Henna", http://www.thehennaqueen.com/how-to-mix-henna.html, published May 7, 2016.

Jamila, "Jamila Henna Powder, 100 grams", https://www.amazon.com/Jamila-Henna-Powder-100-grams/dp/B006K3TZS4, posted for sale on Amazon at least as early as May 15, 2014.

"Xeloda side effects: Henna tip for Hand-Foot Syndrome (HFS or PPE)", http://xelodasideeffects.blogspot.com/2008/07/all-about-henna.html, Jul. 2008.

Yucel, Idris and Guzin, Gonullu, Topical Henna for Capecitabine Induced Hand-Foot Syndrome, https://www.researchgate.net/publication/5957032_Topical_henna_for_capecitabine_induced_hand-foot_syndrome, published online Sep. 21, 2007.

Side #1: Soft/absorbent microfiber towel        Side #2: Scrubbing textured ridges

MEDICINAL COMPOSITION, METHOD OF MANUFACTURE, AND METHOD FOR TREATING SKIN AILMENTS SUCH AS PALMAR-PLANTAR ERYTHRODYSESTHESIA

TECHNICAL FIELD

The present invention relates to medicinal compositions and related methods, including a method for manufacturing the medicinal composition and a method of applying the medicinal composition for treating pain, more particularly for treating pain induced by chemotherapy directly inducing HFS (hand and foot syndrome) or palmar plantar erythrodysesthesia with Lawsone (2-hydroxy-1,4-naphthoquinone) as monotherapy or in combination with other compounds. The medicinal composition may also be used for treating other skin ailments.

BACKGROUND

On Apr. 10, 2017 my wife and co-inventor, Laura Allio, was diagnosed with Stage 2B triple Negative Breast Cancer. She underwent four separate chemotherapy regimens (Cytoxan, Adriamycin, Taxol and Capecitabine) and was later diagnosed with severe grade 3 HFS (Grading is 0-4 with grade 4 being most severe and requiring hospitalization.) At the time of onset, our Oncologist recommended a dose reduction in order to reduce this common side effect. However, we refused the option to dose reduce and potentially lose the valuable efficacy of the chemotherapies.

We began searching for remedies that could reduce the painful swelling, cool the burning, blistering and cracking of her hands and feet and improve her overall quality of life. Frustrated with the lack of options and unsatisfied with the relief she felt with prescription and OTC remedies, we created a topical formulation which, when applied once a day, cooled the skin and routinely reduced her pain score by 75% over the span of 24 weeks.

Unfortunately, my wife lost her courageous battle with breast cancer on Jan. 23, 2019. Throughout the past two years, Saint James Therapeutics has developed multiple formulations that effectively combat HFS, improve the quality of life of those needing it most and deliver these remedies at a cost-conscious price point.

Saint James Therapeutics is seeking to protect its current and future formulations so that it can further develop and improve upon what we believe will not only reduce the discomfort of HFS but also improve the likelihood that patients complete their physician-recommended chemotherapy schedule.

Hand-foot syndrome (HFS) is a side-effect of chemotherapy and other medicines used to treat breast and colorectal cancers. This skin reaction is triggered when some amount of the medicine seeps out of the skin cells or capillaries on the soles of the feet or palms. HFS causes redness, swelling and intense pain in these areas and in some cases, can also lead to blisters.

There are a number of chemotherapy drugs that are known for causing palmar-plantar erythrodysesthesia. Some of the more common drugs for causing this condition include Docetaxel, Doxorubicin, Xeloda, Doxil and Nexavar. Other chemotherapy drugs that cause this condition include Cytosar-U, Adrucil, Floxuridine, Idamycin, Taxol, Zelboraf, Inlyta, Cabometyx, Stivarga, Sutent, Votrient, Inlyta, Cabometyx and Stivarga.

It is estimated that more than 619,959 patients receiving a chemotherapy agent known to cause HFS, 158,033 patients will get HFS annually within the United States and proactively seek out a treatment to offset this painful side effect.[4] Currently, the standard of therapy to combat HFS is dose reduction of chemotherapy, coadministration of prescription NSAIDs or steroids or OTC medications that either reduce the efficacy of the chemotherapy regimen or fail to adequately alleviate the painful blistering that occurs when small amounts of chemotherapy medication leaks outside of the capillaries and cause damage to exposed tissue in the patient's hands and feet.

Symptoms of hand and foot syndrome include redness similar in nature to a sunburn, swelling, a sensation of tingling or burning, tightness of the skin, and thick calluses and blisters on the palms of the hands and the soles of the feet. Other symptoms of hand and foot syndrome include an over sensitivity to touch, pressure and hot and cold temperatures. More severe symptoms of this condition include cracked, flaking or peeling skin; blisters, ulcers or sores on the skin; severe pain; and difficulty walking and using one's hands. Patients who experience this condition are in a constant state of pain throughout the day. Daily tasks involving the use of the hands and feet such as opening containers, touching and lifting items, driving and walking can cause significant distress to the patient due to an unbearable pain which makes simple tasks impossible to accomplish.

Currently, other than applying moisturizers and certain over the counter products, there not many options for treating palmar-plantar erythrodysesthesia. Accordingly, physicians often treat palmar-plantar erythrodysesthesia by reducing the amount of chemotherapy treatments for the cancer patient. However, reducing the amount of chemotherapy treatments is not always a good option depending on how aggressive the cancer is and what stage cancer the patient has. Also, reducing chemotherapy does not provide immediate relief for hand and foot syndrome. Table 1, provided below, lists current recommend chemotherapy treatment adjustments for patients suffering from HFS.

TABLE 1

Current Recommended Dose Modifications for Hand-Foot Syndrome[5]

| Toxicity | Dose Adjustment |
|---|---|
| Hand-Foot Syndrome (HFS) | |
| Grade 1: Mild erythema, swelling, or desquamation not interfering with daily activities | If no previous Grade 3 or 4 HFS: no dose adjustment. If previous Grade 3 or 4 HFS: delay dose up to 2 weeks, then decrease dose by 25%. |

TABLE 1-continued

Current Recommended Dose Modifications for Hand-Foot Syndrome[5]

| Toxicity | Dose Adjustment |
| --- | --- |
| Grade 2: Erythema, desquamation, or swelling interfering with, but not precluding normal physical activities; small blisters or ulcerations less than 2 cm in diameter | Delay dosing up to 2 weeks or until resolved to Grade 0-1. Discontinue doxorubicin hydrochloride liposome injection if no resolution after 2 weeks. If resolved to Grade 0-1 within 2 weeks: And no previous Grade 3 or 4 HFS: continue treatment at previous dose. And previous Grade 3 or 4 toxicity: decrease dose by 25%. |
| Grade 3: Blistering, ulceration, or swelling interfering with walking or normal daily activities; cannot wear regular clothing | Delay dosing up to 2 weeks or until resolved to Grade 0-1, then decrease dose by 25%. Discontinue doxorubicin hydrochloride liposome injection if no resolution after 2 weeks. |
| Grade 4: Diffuse or local process causing infectious complications, or a bed ridden state or hospitalization | Delay dosing up to 2 weeks or until resolved to Grade 0-1, then decrease dose by 25%. Discontinue doxorubicin hydrochloride liposome injection if no resolution after 2 weeks. |

Other treatment options for patients suffering from HFS are relatively rudimentary and oftentimes do not provide adequate relief from the pain experienced from individuals suffering from this condition. Breastcancer.org has published the following guidelines for treating individuals suffering from HFS.

Current medical guidelines published by BreastCancer.org[7] for managing chemotherapy-induced hand-foot syndrome are as follows:
 Apply ice packs wrapped in a towel or packages of frozen vegetables to the affected area(s) to help cool the burning sensation.
 Elevate your hands and feet when you're sitting or lying down.
 Pat your skin dry. Rubbing with a towel can be irritating.
 Keep your hands and feet moist by using mild skin creams. Try to pat the lotion into your skin—rubbing it in too vigorously can cause friction.
 Wear slippers or other loose, well-ventilated shoes. Don't wear shoes that are too tight or rub on your feet.
 Stay away from harsh chemicals such as laundry detergents or cleaning products, which could make the condition worse.
 Talk to your doctor about lowering your chemotherapy dose or changing your treatment schedule. Your doctor may temporarily stop your treatment until your symptoms improve. Your doctor may also prescribe corticosteroids that you can take by mouth or apply to the skin in order to reduce inflammation. You also can ask your doctor if taking pain relievers such as acetaminophen (a brand name: Tylenol) might help ease any discomfort you have.
 Try using a 10% urea cream on your hands and feet. A study found that applying a 10% urea cream three times per day, plus after handwashing, helped prevent hand-foot syndrome for the first 6 weeks of treatment in people taking Capecitabine.

While usually palliative care or supportive treatment along with topical anesthetics is used to treat HFS, a study has found that topically applying Henna to the affected areas can be effective in providing relief from this side-effect.[6]

For centuries, Henna (Lawsonia inermis, 2-hydroxy-1,4-naphthoquinone, hennotannic acid) has been studied extensively by researchers and scientists alike attempting to unlock the therapeutic benefits of this ancient plant. Historically, Henna has been used as a topical cosmetic to decorate the human skin as it possesses staining properties that temporarily dye the skin dark red or brown in shade. Popular with Indian, Pakistani and Hindi cultures, Henna is most often seen in traditional body art (mehndi) at weddings, festivals and other significant Hindi celebrations.

It has long been believed that Henna can offer significant therapeutic benefits such as possessing anti-inflammatory, hypotensive, antibacterial, antimicrobial, astringent, and antiviral effects.

One significant obstacle that has kept Henna from inclusion into health care products has much to do with Henna's farming practices. Unlike other organic botanicals grown to be used in consumer products, farming Henna continues to this day to have minimal oversight and lacks standardization which presents the FDA with questions about the plant's identity, origin, quality, purity, and consistency. All of which are fundamental to protecting public health. To date, Henna does not possess a United States Pharmacopeia (USP) certification due to crop variance. In addition, foreign grown Henna may contain harmful pesticides that can produce negative side effects such as skin burns, rashes and allergic reactions.

The FDA allows Henna to be used as a hair dye [10 FDA § 73.2190] to be applied on the scalp. However, Henna has yet to gain approval from the FDA for use directly on the skin. Popular consensus believes that is due to the variance in biological properties contained within Henna itself and particularly the dangers of "Black Henna." Since Henna is a natural plant grown in diverse climates and ecosystems throughout the world, the growing process and chemical makeup of Henna can vary depending on location, climate, soil conditions and farming techniques. Equally important, Henna growing has and continues to be an unregulated practice that will present the FDA with doubt and therefore potentially keep the plant's medicinal benefits restricted from researchers, drug developers, health care providers and most importantly the patients that need it most.

What is therefore needed is a medication for treating palmar-plantar erythrodysesthesia which eliminates or reduces the pain and burning sensations, which allows cancer patients to continue on a recommended chemotherapy treatment plan to treat their cancer and which allows patients to carry on with their normal day to day activities without experiencing disabling pain.

SUMMARY

Provided is a medicinal composition for treating palmar-plantar erythrodysesthesia and other skin conditions. According to certain aspects of the present teaching, the medicinal composition includes a combination of the Lawsone molecule and a glycoside which activates the analgesic properties of the Lawsone molecule.

Also provided is a method of making a medicinal composition for treating palmar-plantar erythrodysesthesia and other skin conditions which includes the following steps: adding ⅔ of a cup of aloe juice to a pot; heating the pot to bring the aloe juice to a boil; reducing the heat to allow the aloe juice to simmer; adding one-half cup of Henna to the aloe juice; mixing the Henna and aloe juice; adding one teaspoon of lemon juice, one tablespoon of coconut oil and eight drops of each of tea tree oil, *eucalyptus* oil and frankincense; removing the pot from the heat and mixing its contents; adding water as necessary to obtain the desired consistency to form a liquid, paste or cream; and storing the liquid, paste or cream in a container in a refrigerator.

Also provided is a method of administering a medicinal composition palmar-plantar erythrodysesthesia and other skin conditions which includes the following steps: applying the medicinal composition to the hands and feet or other affected areas of a patient; waiting approximately 10 to 15 minutes for the medicinal composition to dry and form a mask or film on the patient's hands and feet; and washing the medicinal composition off from the patient's hands and feet using water. The method may also include the step of applying a moisturizer to the patient's hands and feet after washing the medicinal composition off. The method may also include the step of the patient bathing his or her hands and feet in an Epsom salt bath after applying the moisturizer.

Also provided is a topical treatment medicinal composition. The topical treatment medicinal composition includes a Lawsone molecule, wherein the Lawsone molecule includes the following chemical structure, Lawsone Molecule and a glycoside, wherein the glycoside includes the following chemical structure, Glycoside wherein the glycoside comprises an aglycone (genin) bound to a glycone sugar, wherein the glycoside is formed by combining sugars, fruit acids and/or uronic acids with the aglycone group, wherein the Lawsone molecule comprises analgesic properties, and wherein the analgesic properties of the Lawsone molecule are activated by combining the Lawsone molecule with the glycoside.

According to certain aspects of the present teaching, the glycoside is selected from the group consisting of Anthraquinones glycosides, Cardiac glycosides, Saponin glycosides, Tetracyclic Triterpenoids saponins, Pentacyclic Triterpenoid saponins, Coumarin and furocoumarin glycosides, Cyanophore glycosides, Flavonoids glycosides, Flavone glycosides, Flavonol glycosides, FlacanOne glycosides, Chalone glycosides, Isoflavonoid glycoside, Anthocyanidin glycosides, Isothiocyanate glycosides, Phenol glycoside, Aldehyde glycosides, Bitter glycosides and combinations thereof.

According to further aspects of the present teaching, the topical treatment medicinal composition further includes a topical steroid, wherein the topical steroid is selected from the group consisting of betamethasone dipropionate 0.05%, clobetasol propionate 0.05%, diflorasone diacetate 0.05%, fluocinonide 0.1%, flurandrenolide 4 mcg/m2, halobetasol 0.05%, amcinonide ointment 0.1%, desoximetasone, diflorasone diacetate 0.05%, halcinonide 0.1%, amcinonide 0.1%, fluticasone propionate 0.005%, triamcinolone acetonide 0.5%, betamethasone valerate, desoximetasone 0.05%, hydrocortisone 17-butyrate 0.1%, hydrocortisone probutate 0.1%, hydrocortisone valerate 0.2%, fluocinolone acetonide 0.025%, fluticasone propionate 0.05%, mometasone furoate 0.1%, triamcinolone acetonide 0.025%, triamcinolone acetonide 0.1%, alclometasone dipropionate 0.05%, desonide 0.05%, fluocinolone acetonide 0.01%, hydrocortisone 1%, 2.5%, diflorasone topical, prednicarbate topical, clocortolone topical, halcinonide topical, fluocinolone topical, fluticasone topical, amcinonide topical, ammonium lactate/halobetasol topical, mometasone topical, clobetasol topical, flurandrenolide topical, desonide topical, betamethasone topical, desoximetasone topical, fluocinonide topical, prednisolone, dexamethasone, prednisone, triamcinolone, prednisolone, methylprednisolone, budesonide, triamcinolone, dexamethasone, cortisone, deflazacort and combinations thereof.

According to further aspects of the present teaching, the topical treatment medicinal composition further includes a topical nonsteroidal anti-inflammatory drug, wherein the nonsteroidal anti-inflammatory drug is selected from the group consisting of diclofenac/misoprostol systemic, capsaicin/diclofenac topical, trolamine salicylate, naproxen, ibuprofen, aspirin and combinations thereof.

According to further aspects of the present teaching, the topical treatment medicinal composition further includes an antiarrhythmic, wherein the antiarrhythmic is selected from the group consisting of Lidocaine, quinidine, procainamide, phenytoin, flecainide, disopyramide, tocainide, acebutolol, propranolol, propranolol, esmolol, amiodarone, dofetilide, sotalol, dronedarone, ibutilide, diltiazem, verapamil, adenosine and combinations thereof.

According to further aspects of the present teaching, the topical treatment medicinal composition further includes aloe vera.

According to further aspects of the present teaching, the topical treatment medicinal composition further includes an active ingredient selected from the group consisting of glucosamine sulfate, *Boswellia*, hyaluronic acid, rutin, MSM, trypsin, bromelain, chondroitin sulfate, glucosamine HCL, curcumin, turmeric, resveratrol, polyphenol classes, UC-II Collagen, Black pepper extract, 5-Loxin, Calcium, horsetail leaf extract, omega-3 fatty acids, Vitamin C, cetyl myristoleate, Gelatin, silicon dioxide, titanium dioxide, magnesium stearate, amitriptyline, nortriptyline, duloxetine, venlafaxine, willow bark, clover, prickly ash bark, *Corydalis yanhusuo*, *lobelia*, California poppy, metformin, carbamazepine, topiramate, pregabalin, gabapentin, duloxetine, desvenlafaxine, amitriptyline, azathioprine, cyclosporine, melatonin, fish oil, *ginseng* root, *Ginkgo biloba* extract, coenzyme Q10, St. John's Wort, S-adenosyl methionine, hypericin, pseudohypericin, xanthones, folic acid, vitamin B6, vitamin B12, Butterbur, cayenne, Zyflamend, acetaminophen, vitamin K, Epsom salt, proline, glycine, glutamine, phosphorus, silicon, Sulphur, Earl Grey, *Tanacetum parthenium*, *Filipendula ulmaria*, *Boswellia serrata*, *Harpagophytum procumbens*, *Alpinia officinarum Uncaria tomentosa*, *Foeniculum vulgare*, *Origanum vulgare* ssp. *Hirtum*, *Rosmarinus officinalis*, *Thymus vulgaris*, *Antelaea azadirachta*, *Azadirachta indica*, *Melia azadirachta*, *Rumex crispus*, *Crocus sativus*, *Passiflora incarnata*, *Pedicularis canadensis*, *Lactuca virosa*, *Curcuma longa*, *Tabebuia avellanedae*, *Bupleurum* spp., *Commiphora mukul*, *Yucca* spp., *Dioscorea villosa*, *Salix caprea*, flower of water hyacinth, Flower of Henna (fragrance), Bitter Orange, Sweet Orange, Vanilla and combinations thereof.

According to further aspects of the present teaching, the topical treatment medicinal composition further includes a topical emollient selected from the group consisting of urea, glycerol, propylene glycol, lactic acid, lanolin, liquid paraffin wax, aloe vera topical, glycerin topical, salicylic acid/urea topical, vitamin a & d topical, ammonium lactate topical, emollients topical, ammonium lactate/urea topical, hydrocortisone/urea topical, lactic acid/urea topical, petrolatum topical, vitamins a, d, and e topical, aquaphor, bag balm, dimethicone and combinations thereof.

According to further aspects of the present teaching, the topical treatment medicinal composition further includes a carrier oil, wherein the carrier oil is selected from the group consisting of Coconut Oil, Jojoba Oil, Shea Butter, primrose oil, *arnica* oil, argan oil, rosehip seed oil, tamanu oil, avocado oil, grape seed oil, safflower oil, sunflower oil, vegetable oil, canola oil and combinations thereof.

According to further aspects of the present teaching, the topical treatment medicinal composition further includes an essential oil, wherein the essential oil is selected from the group consisting of Peppermint, Frankincense, Menthol, Spearmint, Wintergreen, Copaiba, Chamomile, Lavender, Marjoram, *Eucalyptus*, Rosemary, Thyme, Coconut Oil, Olive Oil, Clary Sage, Sandalwood, Juniper, Ginger, Yarrow, Vetiver, Helichrysum, Black Pepper Oil, Lemongrass, Rose geranium, Bergamot, Clove, Jojoba, Sweet Almond and combinations thereof.

According to further aspects of the present teaching, the Lawsone molecule is obtained from about 30 to about 50 grams Henna; the glycoside is obtained from about 0.16 to about 0.6 fluid ounces of apple juice, lemon juice, lime juice, orange juice and grapefruit juice, cream of tartar or bitter almonds, and the topical treatment medicinal composition includes about 0.2 to about 0.4 fluid ounces of one of at least three essential oils selected from tea tree oil; *eucalyptus* oil; frankincense; and lavender.

According to further aspects of the present teaching, the topical treatment medicinal composition further includes from about 0.16 to about 0.6 fluid ounces of coconut oil and from about 4.8 to about 5.6 fluid ounces of aloe juice.

According to further aspects of the present teaching, the topical treatment medicinal composition further includes from about 0.2 to about 0.4 fluid ounces of tea tree oil, from about 0.2 to about 0.4 fluid ounces of *eucalyptus* oil and from about 0.2 to about 0.4 fluid ounces of frankincense.

According to further aspects of the present teaching, the form of Henna utilized is selected from the group consisting of Jamila Henna, Cassisa Henna, Indigo Henna and Amla Henna.

Also provided is a method of making a topical treatment medicinal composition. The method includes the following steps: adding ⅔ of a cup of aloe juice to a pot; heating the pot to bring the aloe juice to a boil; reducing the heat to allow the aloe juice to simmer; adding one-half cup or from about 30 to about 50 grams of Henna to the aloe juice; mixing the Henna and aloe juice; adding from about 0.16 to about 0.6 fluid ounces of lemon juice, from about 0.16 to about 0.6 fluid ounces of coconut oil and from about 0.4 to about 0.6 fluid ounces of each of tea tree oil, *eucalyptus* oil and frankincense; removing the pot from the heat and mixing its contents; adding water as necessary to obtain the desired consistency to form a liquid, paste or cream; and storing the liquid, paste or cream in a container in a refrigerator.

Further provided is a method of administering the topical treatment medicinal composition. The method includes the following steps: applying the medicinal composition of claim 1 to the affected areas of a patient requiring treatment; waiting approximately 10 to 15 minutes for the medicinal composition to dry and form a mask or film on the patient's hands and feet; and washing the medicinal composition off from the patient's hands and feet using water.

According to further aspects of the present teaching, the method includes the step of applying a moisturizer to the patient's hands and feet after washing the medicinal composition off.

According to further aspects of the present teaching, the moisturizer includes urea cream, bag balm or utter cream.

According to further aspects of the present teaching, the method includes the step of the patient bathing his or her hands and feet or treated areas in an Epsom salt bath after applying the moisturizer.

Also provided is a delivery system for administering the topical treatment medicinal composition. The delivery system includes one of the following: a pump bottle, an aerosol spray, a roll-on applicator, a tray, a mask applicator, and a transdermal patch, wherein the transdermal patch is one of a microreservoir type or microsealed dissolution-controlled system, a membrane permeation system, an adhesive dispersion-type system, and a matrix diffusion-controlled system.

DETAILED DESCRIPTION

Provided is a medicinal composition for treating skin ailments associated with palmar-plantar erythrodysesthesia (hand and foot syndrome) and other medical ailments. The medicinal composition is directed to a topical skin treatment which functions as an alternative to many commercially available skin therapies used to reduce the painful side effects of palmar-plantar erythrodysesthesia also known as hand and foot syndrome (HFS). The topical skin treatment medicinal composition originates from the Henna plant. The Henna plant contains a chemical compound 2-hydroxy-1,4-naphthoquinone within its leaves. This compound is believed to possesses natural analgesic and skin cooling properties that when combined with other natural and synthetic compounds creates an efficacious and safe, non-opioid topical therapy for those suffering from HFS as well as other painful skin diseases and neurological conditions.

The topical skin treatment medicinal composition is obtained by extracting 2-hydroxy-1,4-naphthoquinone from Henna leaves and activating its analgesic properties by combining it with a synthetically created glycoside. It's important to note that 2-hydroxy-1,4-naphthoquinone by itself will not deliver analgesia and that it must be combined with another agent to activate its analgesic benefits.

The primary application of the topical skin treatment is that it is to be used on patients suffering from chemotherapy-induced HFS. However, it may also be used to effectively treat many skin conditions such as sunburn, diabetic neuropathy, heat rashes, heat blisters, radiation burns, chemical burns, electrical burns, wet burns caused by steam or hot liquids, poison ivy, oak and sumac and other common and uncommon skin irritations derived from disease, medication side effects, allergic reactions, environmental causes or other painful skin conditions requiring cooling relief, analgesia and tissue repair. In addition, the topical treatment medicinal composition may also be used to treat generalized pain, for example, to treat pain associated with any condition. An example of a condition the topical treatment medicinal composition may be use for includes but is not limited to fibromyalgia.

According to certain embodiments, the topical skin treatment medicinal composition is made by combining the Lawsone molecule with a synthetically created glycoside as shown below.

The first step of the process involves synthetically manufacturing Lawsone (2-hydroxy-1,4-naphthoquinone) in a controlled laboratory setting to ensure purity through column chromotography. Lawsone may also be purchase by a chemical bulk wholesaler. Next, Lawsone's analgesic properties are activated by combining it with a glycoside (Glycoside=Aglycone (genin)+Glycone (sugar)) (see above diagram as an example). The differing types of glycosides used in combination with Lawsone may include any of the following: Anthraquinones glycosides, Cardiac glycosides, Saponin glycosides, Tetracyclic Triterpenoids saponins, Pentacyclic Triterpenoid saponins, Coumarin and furocoumarin glycosides, Cyanophore glycosides, Flavonoids glycosides, Flavone glycosides, Flavonol glycosides, FlacanOne glycosides, Chalone glycosides, Isoflavonoid glycoside, Anthocyanidin glycosides, Isothiocyanate glycosides, Phenol glycoside, Aldehyde glycosides, Bitter glycosides and combinations thereof.

To create the glycoside, sugars, fruit acids and/or uronic acids are combined with the Aglycone group. The types of Glycones which may be used within our formulation may include: Malic acid or alpha hydroxyl acid (lower incidence of skin irritation), Citric Acid, Tartaric Acid and Mandelic Acid, low level of increased irritation to the skin).

The glycoside is then combined with pure Lawsone (2-hydroxy-1,4-naphthoquinone) to activate Lawsone's analgesic properties and create a concentrated suspension. The suspension may then be combined with other inactive and/or active ingredients to provide complimentary and synergistic therapeutic benefits to improve texture, scent, stability, longevity and pain reducing efficacy.

The topical skin treatment medicinal composition may include other ingredients and additives in addition to Lawsone and glycoside.

According to certain aspects of the present teaching, the topical skin treatment medicinal composition may include common topical steroids. Examples of common topical steroids which may be included within the medicinal composition include but are not limited to betamethasone dipropionate 0.05%, clobetasol propionate 0.05%, diflorasone diacetate 0.05%, fluocinonide 0.1%, flurandrenolide 4 mcg/m2, halobetasol 0.05%, amcinonide ointment 0.1%, desoximetasone, diflorasone diacetate 0.05%, halcinonide 0.1%, amcinonide 0.1%, fluticasone propionate 0.005%, triamcinolone acetonide 0.5%, betamethasone valerate, desoximetasone 0.05%, hydrocortisone 17-butyrate 0.1%, hydrocortisone probutate 0.1%, hydrocortisone valerate 0.2%, fluocinolone acetonide 0.025%, fluticasone propionate 0.05%, mometasone furoate 0.1%, triamcinolone acetonide 0.025%, triamcinolone acetonide 0.1%, alclometasone dipropionate 0.05%, desonide 0.05%, fluocinolone acetonide 0.01%, hydrocortisone 1%, 2.5%, diflorasone topical, prednicarbate topical, clocortolone topical, halcinonide topical, fluocinolone topical, fluticasone topical, amcinonide topical, ammonium lactate/halobetasol topical, mometasone topical, clobetasol topical, flurandrenolide topical, desonide topical, betamethasone topical, desoximetasone topical, fluocinonide topical, prednisolone, dexamethasone, prednisone, triamcinolone, prednisolone, methylprednisolone, budesonide, triamcinolone, dexamethasone, cortisone, deflazacort and combinations thereof.

According to certain aspects of the present teaching, the topical skin treatment medicinal composition may include topical nonsteroidal anti-inflammatory drugs (NSAIDS). Examples of NSAIDS which may be included within the medicinal composition include but are not limited to diclofenac/misoprostol systemic, capsaicin/diclofenac topical, trolamine salicylate, naproxen, ibuprofen, aspirin and combinations thereof.

According to certain aspects of the present teaching, the topical skin treatment medicinal composition may include antiarrhythmics. Examples of antiarrhythmics which may be included within the medicinal composition include but are not limited to Lidocaine, quinidine, procainamide, phenytoin, flecainide, disopyramide, tocainide, acebutolol, propranolol, propranolol, esmolol, amiodarone, dofetilide, sotalol, dronedarone, ibutilide, diltiazem, verapamil, adenosine and combinations thereof.

According to certain aspects of the present teaching, the topical treatment medicinal composition may include aloe vera.

According to certain aspects of the present teaching, the topical treatment medicinal composition may include capsaicin and other capsaicinoids.

According to certain aspects of the present teaching, the topical skin treatment medicinal composition may include one or more of a variety of active ingredients. Examples of active ingredients which may be included within the medicinal composition include but are not limited to glucosamine sulfate, *Boswellia*, hyaluronic acid, rutin, MSM, trypsin, bromelain, chondroitin sulfate, glucosamine HCL, curcumin, turmeric, resveratrol, polyphenol classes, UC-II Collagen, Black pepper extract, 5-Loxin, Calcium, horsetail leaf extract, omega-3 fatty acids, Vitamin C, cetyl myristoleate, Gelatin, silicon dioxide, titanium dioxide, magnesium stearate, amitriptyline, nortriptyline, duloxetine, venlafaxine, willow bark, clover, prickly ash bark, *Corydalis yanhusuo, lobelia*, California poppy, metformin, carbamazepine, topiramate, pregabalin, gabapentin, duloxetine, desvenlafaxine, amitriptyline, azathioprine, cyclosporine, melatonin, fish oil, *ginseng* root, *Ginkgo biloba* extract, coenzyme Q10, St. John's Wort, S-adenosyl methionine, hypericin, pseudohypericin, xanthones, folic acid, vitamin B6, vitamin B12, Butterbur, cayenne, Zyflamend, acetaminophen, vitamin K, Epsom salt, proline, glycine, glutamine, phosphorus, silicon, Sulphur, Earl Grey, *Tanacetum parthenium, Filipendula ulmaria, Boswellia serrata, Harpagophytum procumbens, Alpinia officinarum Uncaria tomentosa, Foeniculum vulgare, Origanum vulgare* ssp. *Hirtum, Rosmarinus officinalis, Thymus vulgaris, Antelaea azadirachta, Azadirachta indica, Melia azadirachta, Rumex crispus, Crocus sativus, Passiflora incarnata, Pedicularis canadensis, Lactuca virosa, Curcuma longa, Tabebuia avellanedae, Bupleurum* spp., *Commiphora mukul, Yucca* spp., *Dioscorea villosa, Salix caprea*, flower of water hyacinth, Flower of Henna (fragrance), Bitter Orange, Sweet Orange, Vanilla and combinations thereof.

According to certain aspects of the present teaching, the topical skin treatment medicinal composition may include topical emollients. Examples of common topical steroids which may be included within the medicinal composition include but are not limited to urea, glycerol, propylene glycol, lactic acid, lanolin, liquid paraffin wax, aloe vera topical, glycerin topical, salicylic acid/urea topical, vitamin a & d topical, ammonium lactate topical, emollients topical, ammonium lactate/urea topical, hydrocortisone/urea topical, lactic acid/urea topical, petrolatum topical, vitamins a, d, and e topical, aquaphor, bag balm, dimethicone and combinations thereof.

According to certain aspects of the present teaching, the topical treatment medicinal composition may include carrier oils. Examples of carrier oils which may be included within the medicinal composition include but are not limited to Coconut Oil, Jojoba Oil, Shea Butter, primrose oil, *arnica* oil, argan oil, rosehip seed oil, tamanu oil, avocado oil, grape seed oil, safflower oil, sunflower oil, vegetable oil, canola oil and combinations thereof.

According to certain aspects of the present teaching, the topical treatment medicinal composition may include cannabidiol (CBD) and hemp derived oils and extracts.

According to certain aspects of the present teaching, the topical treatment medicinal composition may include essential oils. Examples of essential oils which may be included within the medicinal composition include but are not limited to Peppermint, Frankincense, Menthol, Spearmint, Wintergreen, Copaiba, Chamomile, Lavender, Marjoram, *Eucalyptus*, Rosemary, Thyme, Coconut Oil, Olive Oil, Clary Sage, Sandalwood, Juniper, Ginger, Yarrow, Vetiver, Helichrysum, Black Pepper Oil, Lemongrass, Rose geranium, Bergamot, Clove, Jojoba, Sweet Almond and combinations thereof.

According to further aspects of the present teaching, the Lawsone molecule may be directly extracted from Henna plant instead of being chemically synthesized. One method for extracting Lawsone is described in the article "What is the Best Method to Extract Lawsone Frome Henna" by (See "https://www.researchgate.net/post/What_is_the_best_method_to_extract_lawsone_from_Henna" which is herein incorporated by reference in its entirety). Alternatively, Lawsone may be extracted by a soxhlet extraction technique using methanol solvent as described for example by Mehrdad Mahkam et al. in the article "Isolation, Identification and Characterization of Lawsone from Henna Leaves Powder with Soxhlet Technique", Iranian Chemical Communication, Article 4, Volume 2, Issue 1, pp. 1-81, Winter and Spring 2014 which is herein incorporated by reference in its entirety. The merit of the soxhlet extraction technique is that large amounts of Lawsone may be extracted (e.g., 720 mg from 40 grams of Henna powder) using a small quantity of methanol. The extracted Lawsone may then be optimized using UV-VIS, FT-IR and NMR analysis.[9]

According to further embodiments, the topical skin treatment medicinal composition may be formed from a homemade method from a mixture of Henna, water, fruit juice, and one of the following ingredients-tea tree oil, *eucalyptus* oil, lavender and frankincense. The fruit juice used may be selected according to the acid it provides. For example, apple juice is employed for malic acid and lemon juice is employed for citric acid. As an alternative to fruit juice cream of tartar may be employed for tartaric acid and bitter almonds may be employed for mandelic acid in making the medicinal composition. In certain embodiments, the water may be purified.

According to further embodiments, the medicinal composition may be formed from a home-made method from a mixture of Henna, pure aloe juice, lemon juice, coconut oil, and three essential oils including tea tree oil, *eucalyptus* oil and frankincense. In certain embodiments described below, this composition may also be referred to as the base medicinal composition.

There are many variations of Henna that may be used within the medicinal composition of the present disclosure. By way of background, Henna is typically used as a dye that can be applied to the skin as body art or used as a hair dye. Formation of Henna as a dye involves drying, milling and sifting Henna leaves, mashing the dried Henna leaves into a powder and adding a liquid such as water, lemon juice or a strong tea to form a Henna paste. Organic and pure Henna is recommended but not required for making the medicinal composition. Moreover, while most variety of Henna are completely safe to use, a variety of Black Henna has been known to cause significant allergic reactions causing skin rashes and internal discomfort as experienced by some users. Also, some Henna-based hair products that claim to be pure contain harmful chemicals that can intensify the allergic reactions some people may experience when interacting with impure or black Henna-based products. For example, although *Lawsonia inermis* Linn shows anti-inflammatory, analgesic and antipyretic effects, it may also cause side-effects such as hemolytic anemia in cases of glucose-6-phosphate dehydrogenase enzyme deficiency. However, studies conducted on dye formulations of *Lawsonia inermis* Linn have shown no damage to human hairs, no adverse effects on the scalp and that such dyes may be used for dying silk and cotton fabrics.

Varieties of Henna which may be used in the medicinal composition of the present disclosure include but are not limited to natural Henna, neutral Henna, and black Henna. One brand of Henna that has been shown to be particularly effective is Jamila Henna.

Patients utilizing the medicinal composition disclosed herein experience complete pain relief and burning sensation relief stemming from palmar-plantar erythrodysesthesia or hand and foot syndrome. Without being bound to any particular theory it is believed that ingredients including Henna, lemon juice and water provide an immediate sense of relief from palmar-plantar erythrodysesthesia in terms of relief from the burning sensation on the patient's hands and feet. However, these ingredients leave the patient's skin dry and cause a different type of pain that can be best described as a dry pain which leaves the patient's hands in an immovable state. Therefore, to eliminate this dry pain and improve mobility, other agents were added to the composition. These other agents including aloe juice, coconut oil and essential oils such as tea tree oil, *eucalyptus* oil and frankincense have been shown to be effective in completely eliminate this dry pain and improving mobility. It is believed that these ingredients accomplish these positive effects by acting as moisturizing agents. Excess amounts of these moisturizing ingredients should be avoided as it can result in the medicinal composition becoming too liquidy and not drying on the patient's skin and can prohibit pain relief. Therefore, relatively moderate amounts of these moisturizing ingredients should be used so that the medicinal composition is not rendered ineffective for its intended use as a pain reliever for hand and foot syndrome.

Essential oils such as tea tree oil, *eucalyptus* oil and frankincense are pure oils that are extracted from a leaf. Although the medicinal composition includes tea tree oil, *eucalyptus* oil and frankincense as essential oils, other essential oils may also be used. Essential oils also provide the benefit of providing a pleasant fragrance to the medicinal composition.

Other ingredients which may be included in the medicinal composition disclosed herein or used in conjunction with the medicinal composition disclosed herein include common preservative agents (if needed), Desitin, Differin (e.g., one teaspoon), Preparation H and urea cream, bag balm or utter cream as a separate post-application moisturizer.

The benefits of including Preparation H within the medicinal composition disclosed herein is that it is believed to cause vasoconstriction when applied to areas on the hands and feet which can have a positive effect at reducing the burning sensation and other sensitivities associated with palmar-plantar erythrodysesthesia.

Urea cream has not been shown to be as effective as other ingredients disclosed above at reducing and eliminating pain associated with palmar-plantar erythrodysesthesia. Therefore, urea cream is normally not included as part of the base medicinal composition. However, as described below, urea cream may be used as a component of a moisturizer that is applied after application of the base medicinal composition.

To facilitate the making of the medicinal composition according to the home-made method, a kit may be provided. According to certain aspects of the present teaching, the kit may include individual packets of organic/pure Henna, common preservative agents (if needed), fruit acid, water or purified water, a post-application moisturizer (e.g., 10% to 40% urea cream, bag balm, utter cream or Preparation H), a sunlight protected mixing jar, a mixing spoon and socks or mitts to be worn after the mixture has been applied.

Also provided is a method of making a medicinal composition in the form of a liquid, cream or paste for treating palmar-plantar erythrodysesthesia.

According to a first example, the method includes bringing 1 cup of purified water to a boil; mixing the boiled purified water with about ½ cup or from about 40 to about 60 grams of dry Henna powder (e.g., Jumila, Cassisa, Indigo, Amla) and reducing the heat to a simmer until it forms a thick soupy paste; adding about one teaspoon or about one tablespoon or from about 0.16 to about 0.6 fluid ounces of fruit juice which may be malic acid (apple juice), citric acid (lemon juice, lime juice, orange juice and grapefruit juice), tartaric acid (cream of tartar) or mandelic acid (bitter almonds) to the boiled mixture; removing the paste from the stove top and adding about 0.2 to about 0.4 or about 0.33 fluid ounces of frankincense, lavender, tea tree or *eucalyptus* oil; placing the mixture into a jar; placing the jar in a refrigerator and allowing the mixture to cool for about 2 to about 4 hours. In certain instances, the refrigerator may be set to a temperature ranging from about 0° C. to about 4.4° C. In certain instances, the amount of Henna may range from about 30 to about 50 grams of Henna. In further instances, about ½ cup of Henna may comprise about 40 grams of Henna. In certain instances, the amount of fruit juice may range from about 0.4 to about 0.6 fluid ounces. In further instances, about 1 tablespoon of fruit juice may comprise about 0.5 fluid ounces.

According to a second example, the method includes adding ⅔ of a cup or from about 4.8 to about 5.6 fluid ounces of aloe juice to a pot which is placed on an electric stove top and heated to ¾ heat or from about 137 to about 175° C. on the dial to bring the aloe juice to a boil. Once the aloe juice has come to a boil, the heat is reduced and allowed to simmer. One-half cup or from about 40 to about 60 grams of Henna is then added to the aloe juice and mixed with a spatula. Next, about one teaspoon or about one tablespoon or from about 0.16 to about 0.6 fluid ounces of lemon juice, about one teaspoon or about one tablespoon or from about 0.16 to about 0.6 fluid ounces of coconut oil and eight drops or from about 0.2 to about 0.4 fluid ounces of each essential oil (tea tree oil, *eucalyptus* oil and frankincense) is added to the mixture. The mixture is then removed from the heat on the stovetop and mixed further. If more liquid is needed to obtain the desired consistency, water may be added at this point in the method. The medicinal liquid, cream or paste was then placed in 3-ounce containers (e.g., glass jars) and placed in a household refrigerator to cool down. The refrigerator was kept at a standard operating temperature (from about 0 to about 4.4 degrees Celsius or from about 32 to about 40 degrees Fahrenheit). Refrigerating the medicinal composition assists in preserving the product and extending its shelf life. It also assists in providing the patient with a cooling sensation upon application to relieve the burning sensation caused by palmar-plantar erythrodysesthesia. However, the product may also be stored at room temperature.

To apply the product, one scoops out a light layer of medicinal composition from the container and applies it to the base of one's hands and the base of one's feet. Due to the staining effect of Henna, the patient may wish to have a towel readily available to wipe off any excess composition from any objects that may come in contact with the patient's hands or feet. For example, if applied to the feet, the patient may want to lay a towel under his or her feet to prevent the product from staining the floor. After application, the patient typically waits approximately 10 to 15 minutes for the product to dry. In some cases, the patient may want to allow the product to remain on the treated areas for approximately 45 to 120 minutes. Once dry, the product forms a mask or film on the patient's hands and/or feet or other treated areas. At this point, the patient may wash the product off his or her hands and/or feet with lukewarm water. To do this, the patient may need to first place the treated areas (e.g., the hands and/or feet) within a soaking bowl or tray containing lukewarm water to allow the paste to loosen. A soft microfiber clothe may be used to gently scrub away existing paste from the treated areas. Care may need to be used not to apply excess pressure which could cause further irritation or damage to the skin. Once removed from the skin, a moisturizer such as 10% urea cream, bag balm or utter cream is applied to the treated areas. The patient may then wish to wear socks and/or mittens or gloves for protection after the topical treatment is applied.

Relief from the symptoms of palmar-plantar erythrodysesthesia is felt immediately upon application of the product to the patient's hands and/or feet. The effectiveness of the product is experienced during the drying process. Once the product is dry it stops providing any additional relief from the symptoms of palmar-plantar erythrodysesthesia. Relief is experienced during the time it takes the product to dry on the patient's skin and lasts approximately 24 hours afterward. This allows the patient to walk around and carry on a full day's tasks without inhibition from the symptoms of palmar-plantar erythrodysesthesia. After approximately 24 hours, the patient will begin feeling an increase in pain and burning associated with palmar-plantar erythrodysesthesia at which time the patient may reapply the product for further treatment.

As mentioned above, according to certain embodiments, the medicinal product may be a system comprising the medicinal base composition and a moisturizer. In such embodiments, application of the medicinal product may encompass a two-step process. The first step of the two-step process is to apply the base product as described above to the affected areas of the skin and allow the product to dry after approximately 10 minutes. This is referred to as the cooling step and results in the drying of the patient's skin. Once the base medicinal product cools and dries out on the patient's skin, the patient may add a moisturizer to the areas of the skin treated with the medicinal product. This is the second step of the two-step process and allows the patient to regain mobility within the dried and tightened skin affected by palmar-plantar erythrodysesthesia. A moisturizer which has been shown to be effective in treatment is a combination of urea cream and Preparation H. Any variation of urea cream and Preparation H may be used. According to one embodiment, the composition of Preparation H that provides moisturizing relief includes 71.9% petrolatum, 14% mineral oil, 3% shark liver oil and 0.25% phenylephrine HCL. According to a further embodiment, the composition of urea cream that provides moisturizing relief is urea (40%) cream.

According to further embodiments, a patient may apply a third step after the second moisturizing step of treating the affected areas of the skin in a bath of Epsom salt. An Epsom salt bath has the effect of heling loosen the skin to make it more bendable and moveable. A recommendation duration for an Epsom salt bath is 15 minutes.

According to further embodiments, the medicinal composition may be formed into a dried powder form and refrigerated. To apply, the patient removes the dried powder from the refrigerator and simply adds water to obtain the desired consistency. This process can extend the shelf life of the medicinal product base composition and avoids the incorporation of preservatives into the medicinal product base composition. However, according to other embodiments, the medicinal product base composition may include preservatives depending on the amount of water that is used within the formulation.

Various delivery mechanisms may be used to apply the topical treatment medicinal composition. According to certain embodiments, one may apply a product to a tray for a patient to place his or her hands or feet in. This will allow patients which are overweight or who cannot easily bend forward to easily apply the product to the soles of their feet.

According to further embodiments, the medicinal composition may be applied to a film that is packaged in a rolled-up state. Upon application, the patient unrolls the film to a flattened state and steps on the film to apply the product to the bottom of the patient's feet. This film may be placed in a container in an unrolled flattened state for application to the bottom of the patient's feet if desired.

Other delivery mechanisms include providing the topical treatment medicinal composition in the form of a topical cream, a gel, an ointment, a mask application, a concentrated oil, a condensed spray, a roll-on product and a transdermal patch. For example, the medicinal composition may be provided in the form of a roll-on applicator similar to a deodorant stick or a container with a flip lid or an easily turnable lid (e.g., a lid that contains flanges on its side which can make it easier to turn the lid for patients having difficulty gripping things to due to HFS). Examples of certain delivery systems provided herein are discussed in greater detail below.

Figure 1:
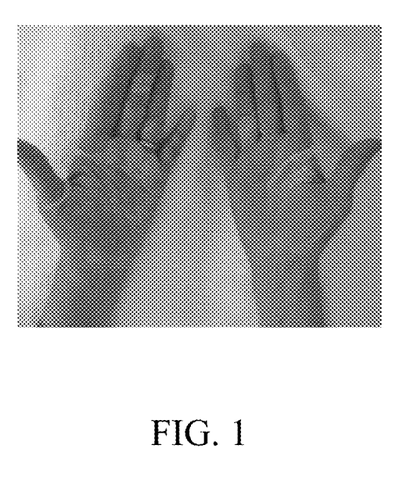
FIG. 1 is an image of a person exhibiting the symptoms of palmar-plantar erythrodysesthesia on her hands.
Figure 2:
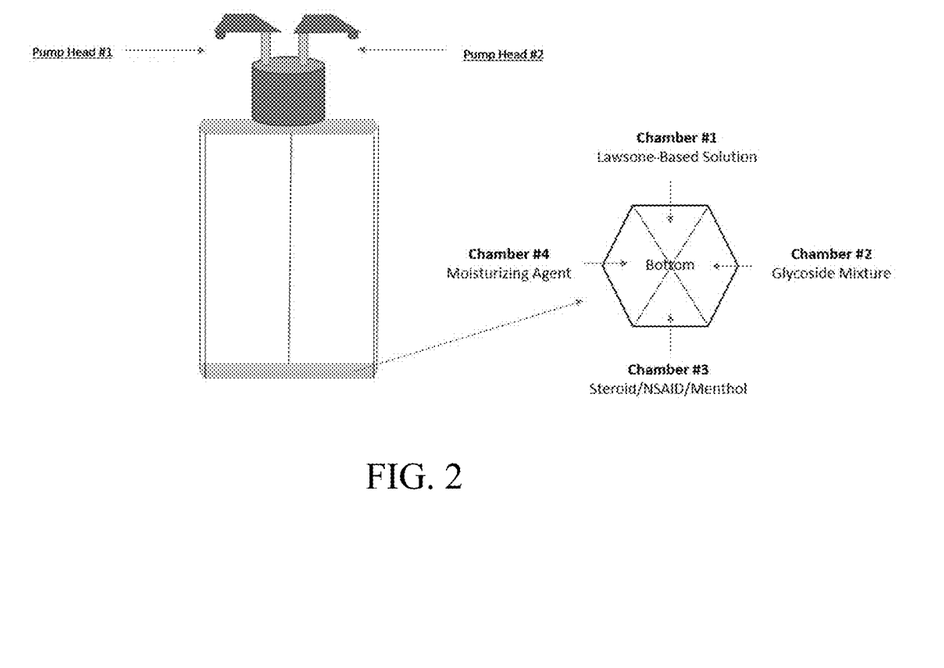
FIG. 2 is an illustration of an exemplary pump bottle which may be used as a medicinal delivery system.

Pump Bottle: In certain applications, the delivery system may be a pump bottle. The pump bottle may be in the form of a container that is capable of protecting the contents contained therein from light and oxygen. The container may contain multiple independent chambers that distributes the products individual ingredients with proper proportion or percentage with a single pump. An example of the distribution of the ingredients within the chambers of the container is shown within FIG. 2 and is as follows: Chamber 1: Henna Mixture (combined with purified water); Chamber 2: Glycoside Mixture; Chamber 3: Independent chamber reserved for additional MOA—Examples include: Corticosteroid, Menthol, Topical NSAID, 4% Lidocaine, Salicylic Acid, Capsaicin; and Chamber 4: Post therapy moisturizer once Henna is removed. The individual ingredients are dispensed independently in the proper dose from the chamber through various pumps in communication with each corresponding chamber (e.g., 4 pumps corresponding to four chambers) and mixed in the hand or in a bowl to prolong shelf life, stability and most accurate concentration of its active ingredients on every application. In certain embodiments, the pump bottle may include a first pump head which accurately dispenses the necessary percentage of each ingredient contained within chambers 1-3 which the consumer may combine within their palm or with the assistance of an approved applicator. The pump bottle may also include a second pump head which can independently distribute a moisturizing agent from chamber 4 once the medication is removed.

Figure 3:
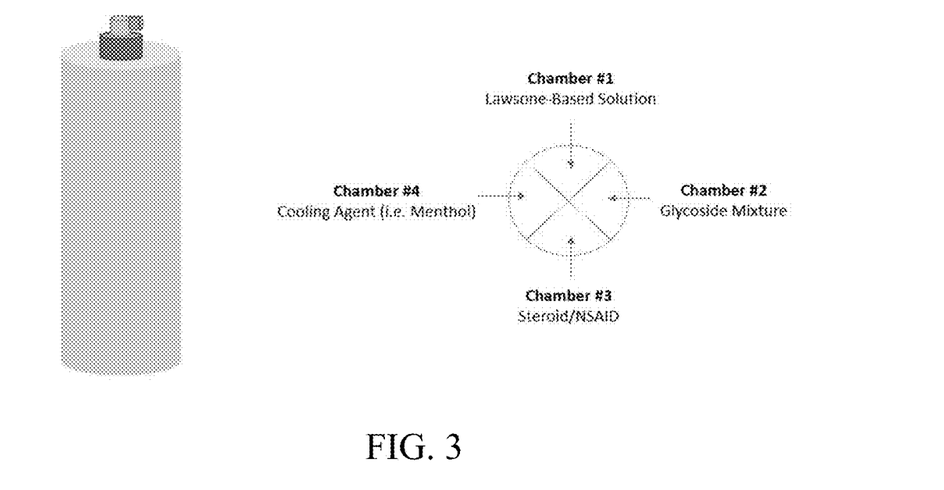
FIG. 3 is an illustration of an exemplary aerosol spray which may be used as a medicinal delivery system.

Aerosol Spray: In further applications, the delivery system may be an aerosol spray. An aerosol spray may be designed to allow for even distribution of the product on affected areas of the skin without requiring application to areas not requiring pain relief. For example, if the foot is the only area affected, then one would not need to apply it onto one's hands in order to achieve relief. The spray would apply a thin layer of the medication onto the surface area of the skin and could be reapplied to achieve maximum effect. An example of an aerosol spray delivery system is shown within FIG. 3. The spray bottle may include 4 different chambers for each of the ingredients of the topical treatment medicinal composition (e.g., chamber 1 for a Lawsone based solution; chamber 2 for a glycoside mixture; chamber 3 for a steroid/NSAID and chamber 4 for a cooling agent). The contents of the each of the chambers may be mixed in proper proportion prior to exiting the nozzle of the spray allowing the user to directly apply the product without having to take any further steps.

Figure 4:
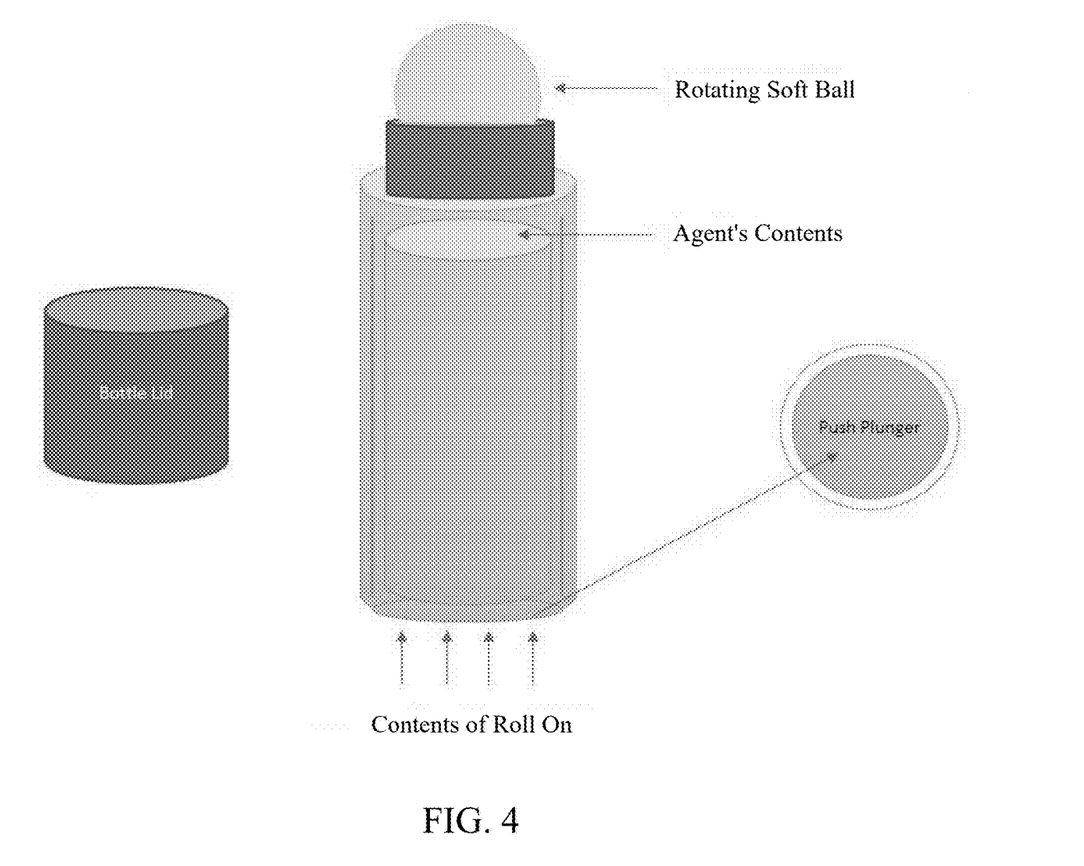
FIG. 4 is an illustration of an exemplary roll-on applicator which may be used as a medicinal delivery system.

Roll-On: In further applications, the delivery system may be a roll-on applicator. An example of a roll-on applicator is illustrated within FIG. 4. The roll-on applicator allows for the topical treatment medicinal composition to either be dispensed via gravity (e.g., by turning the roll-on applicator upside down) or via pressure (e.g., by squeezing or applying pressure to a plunger on the bottom side of the roll-on applicator) which forces the medication to the surface of the roller. FIG. 4 illustrates an example where the contents of the Roll-On are pushed to the surface via a sliding plunger on an inner track located at the bottom of the container of the roll-on. The agent's contents are forced to the surface of a rotating soft ball via a sliding push plunger. The rotating soft ball allows the agent to be distributed evenly without the use of hands. Like the spray applicator, the roll-on applicator also ensures that only the affected areas come into contact with the affected areas that require treatment and avoids unnecessary cross contamination with skin not requiring its therapeutic effect.

Figure 5:
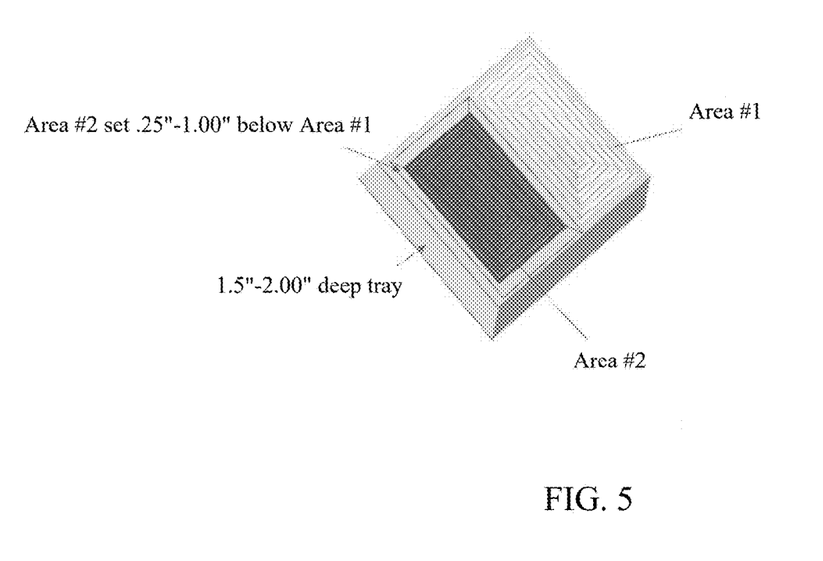
FIGS. 5 and 6 are illustrations of an exemplary tray and mat which may be used as a medicinal delivery system.
Figure 6:
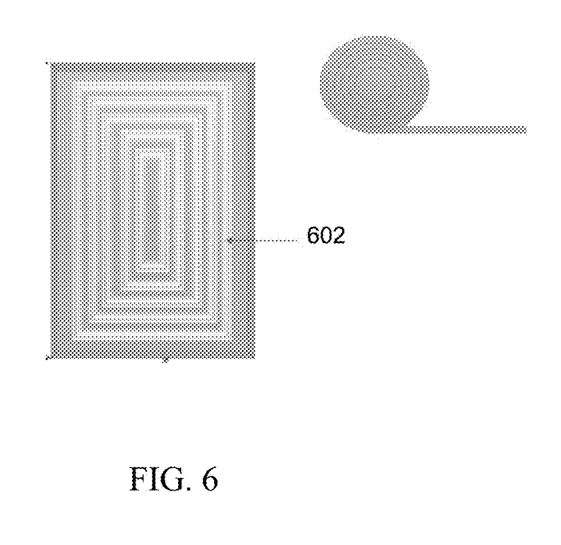

Trays: In further applications, the delivery system may utilize one or more trays. Applying the topical treatment medicinal composition can be incredibly messy. Once applied, it is challenging to avoid getting the product on furniture, clothing and the carpet. Creating designated trays for the hands and feet contains the product, avoids any unnecessary mess and provides the consumer with a designated area to rest their feet and hands while waiting for the therapy to take effect. The trays are reusable and may be made from plastic (polymer based) or gel based (which could also be refrigerated to assist in cooling the affected areas). The gel-based option would look like other beaded cooling applications commonly used to reduce swelling. An example of a tray which may be utilized to as a delivery system is illustrated within FIG. 5. As shown within FIG. 5, the tray may include a replaceable slip resistant mat (e.g., a soft polymer or rubber mat). The tray may also include raised cooling gel ridges for grip and enhanced heel cooling. The level of the mat within the tray may be set slightly below the outside frame of the tray to allow for the contents of the medicinal treatment to be poured in and applied to the heel of the foot. In certain embodiments, the mat is dishwasher safe and is capable of being placed in the freezer of minimum of four hours prior to use. In further embodiments, the mat may also include cooling nodules that can be refrigerated to enhance cooling and improve grip. As shown within FIG. 5, the tray may be divided into two areas referred to as "Area 1" and "Area 2", Area 1 may include a replaceable slip resistant soft polymer mat with raised cooling gel ridges for grip and enhanced heel cooling. This level is set slightly below the outside frame to allow for contents to be poured in and applied to heal the foot. The mat is dishwasher safe. It is recommended that the mat be placed in the freezer for a minimum of four hours prior to use. Area 2 of the tray may include a replaceable rubber/polymer mat located inside a well for the mixture to be poured into and applied. It may also include cooling nodules that can be refrigerated to enhance cooling experience and improve grip. The mat is dishwasher safe. It is recommended that the mat be stored in a freezer for a minimum of four hours prior to use. FIG. 6 illustrates an example of a roll out cooling hand mat which may be placed within the well of the tray. As shown within FIG. 6, cooling gel ridges (602) collect the agent within the spaces and allow for the agent to be cooled and delivered consistently. The mat is set slightly below the frame of the tray which allows the agent to be poured in without escaping. It is recommended that the cooling hand mat be placed in a freezer for a minimum of 4 hours prior to use.

Figure 7:
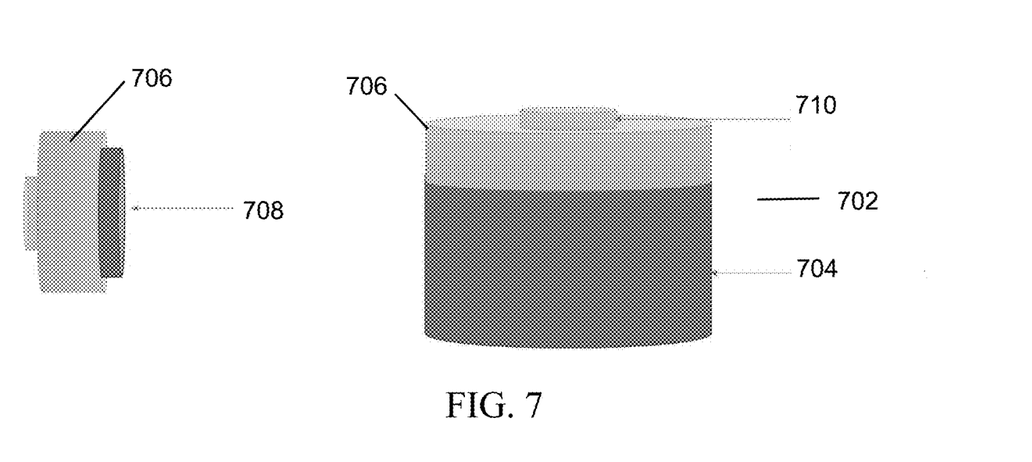
FIGS. 7 and 8 are illustrations of components of an exemplary mask applicator which may be used as a medicinal delivery system.
Figure 8:
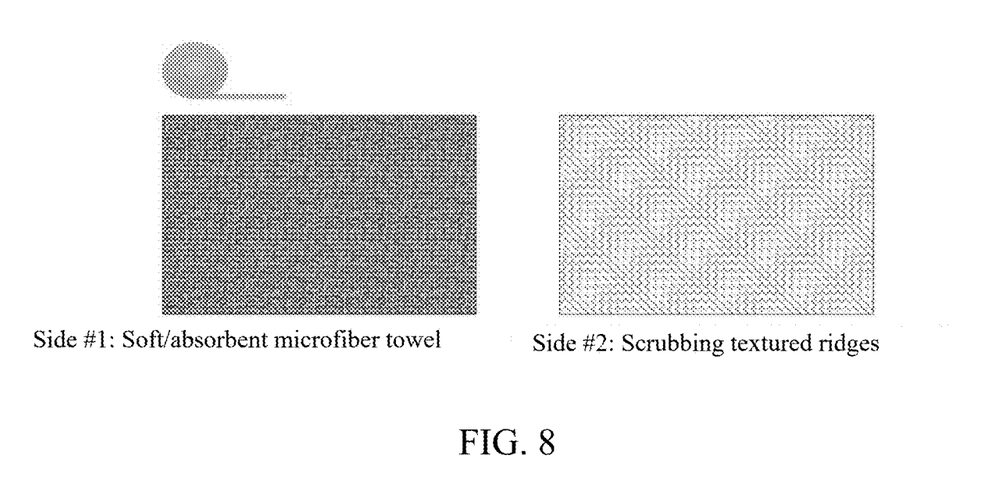

Mask: In further applications, the delivery system may utilize a mask. The mask application takes about 5 to about 10 minutes to activate once applied yet cooling effects can be expected within the first 5 minutes. Once the mask sets, it will harden around the affected areas and should be left on for about another 15 to about 20 minutes. The mask may be removed with cool or lukewarm water and with a microfiber cloth or very soft towel to avoid further scratching to the skin. Once mask is removed, a layer of moisturizer should be applied to restore the necessary oils and water back to the skin. This step will reduce the skins dryness and irritation caused by the mask and will improve future pliability of the skin. The mask application may also be co-administered with breathable socks and gloves that would allow the mask to set and provide the consumer with freedom to navigate their household without the risk of the medication rubbing off. An example of a mask applicator is illustrated within FIG. 7. As shown within FIG. 7, the mask applicator includes a jar (702). The jar includes a main contents chamber (704) and a cap (706). The jar is light protected. On the bottom side of the cap is a soft sponge applicator (708)

which is attached to and located on the inside of the cap. When the jar is shaken, the contents contained therein blend together and coat the internal sponge contained therein. The sponge is used to apply the agent to the affected areas to form a mask thereon. The cap may also include a push down button (710) which pops the cap off via an internal click/locking system to make it easier for people with hand burns to remove the lid and access the contents of the jar. In a further alternative application, socks and mittens or gloves may be internally coated with the medicinal composition with the sponge and can be refrigerated and worn during this process. To remove the mask, a towel is utilized. An example of a towel which may be utilized for this purpose is illustrated within FIG. 8. As shown within FIG. 8, the first side of the towel may include a soft/absorbent microfiber texture that allows for moisture absorption and drying of the skin to aid in removing the topical treatment. The second side of the towel may include textured ridges which allows for scrubbing so that hardened areas of treatment can be easily removed.

Transdermal Patch: In further applications, the topical treatment medicinal composition may be administered via a transdermal patch. In this delivery system, the backing of the patch is breathable in order to allow the wound to heal and also give the medication the necessary oxygen it needs to activate. The formulation is also combined with a light topical adhesive that allows the patch to adhere to the body's movement during routine daily activities. Examples of transdermal delivery systems provided herein are discussed in greater detail below.

Figure 9:
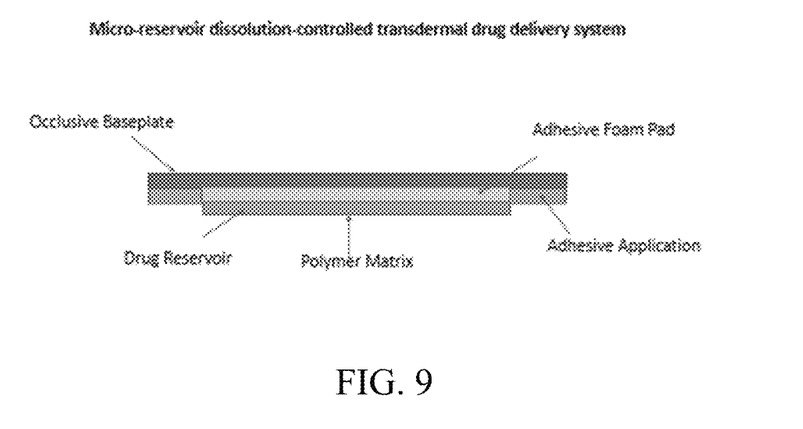
FIG. 9 is an illustration of an exemplary micro-reservoir dissolution-controlled transdermal drug delivery system.

Microreservoir type or microsealed dissolution-controlled systems: In further applications the topical treatment medicinal composition within a microreservoir type or microsealed dissolution controlled system. The drug reservoir is created when the drug is suspended and separated in an aqueous solution of a water soluble liquid polymer and then dispersing the drug suspension homogenously in a lipophilic polymer by high shear mechanical force to form a large number of microreservoirs. These are unleachable microscopic spheres of drug reservoirs. This thermodynamically unstable dispersion is stabilized quickly by immediate addition of cross-linking polymers like Gluteraldehyde the polymer which produces a medicated polymer disc with a constant surface area and a fixed thickness. A transdermal therapeutic system is produced by positioning the medicated disc at the center and surrounding it with an adhesive rim and then it is spread on to the occlusive base plate with adhesive foam pad.[8] An example of a micro-reservoir dissolution-controlled transdermal drug delivery system is illustrated within FIG. 9.

Figure 10:
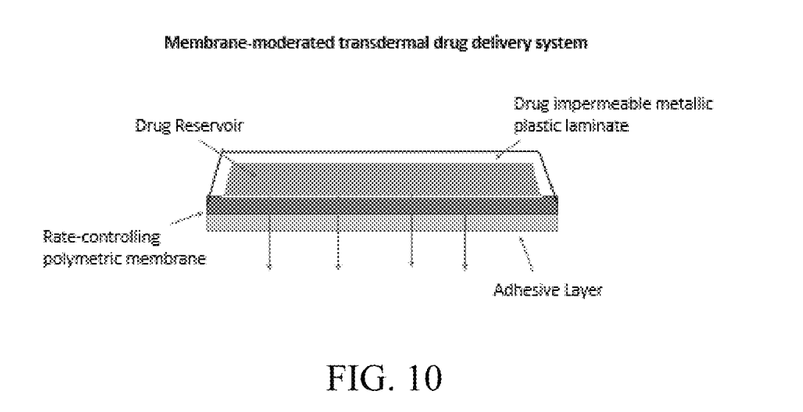
FIG. 10 is an illustration of an exemplary membrane-moderated transdermal drug delivery system.

Membrane Permeation Controlled Systems: Under this variation of a transdermal drug delivery system, the active medication (i.e. Lawsone, Menthol, Hydrocortisone mixture) is placed within the reservoir and is entirely condensed in a shallow compartment molded from a drug impermeable metallic plastic laminate and a rate controlling polymeric membrane (i.e. Ethylene vinyl acetate) with defined drug permeability. The medication's active drug molecules are permitted to release only through the rate-controlling membrane. Within the reservoir, the drug solids are either dispersed in a solid-polymer matrix or suspended in a viscous liquid medium to form a paste like suspension. A thin layer of adhesive polymer is applied to the external surface of the rate-controlling membrane to achieve an intimate contact of the transdermal system and the skin surface.[8] An example of a membrane-moderated transdermal drug delivery system is illustrated within FIG. 10.

Figure 11:
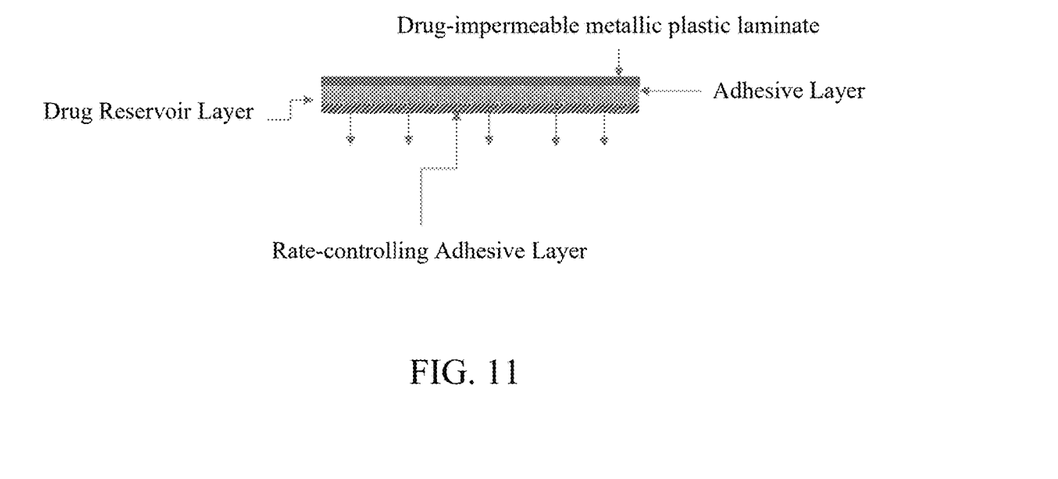
FIG. 11 is an illustration of an exemplary adhesive dispersion-type transdermal drug delivery system.

Adhesive Dispersion-Type System: This transdermal drug delivery system is a simplified form of the membrane permeation-controlled system. The drug reservoir is formulated by directly dispersing the drug (Lawsone plus additives) in an adhesive polymer such as a polyisobutylene and then spreading the medicated adhesive, by solvent casting or hot melt onto a flat sheet of drug impermeable metallic plastic backing to form a thin drug reservoir layer. On the top of the drug reservoir layer, thin layers of non-medicated, rate-controlling adhesive polymer of a specific permeability are applied to produce an adhesive diffusion-controlled delivery system.[8] An example of an adhesive dispersion-type transdermal drug delivery system is illustrated within FIG. 11.

Figure 12:
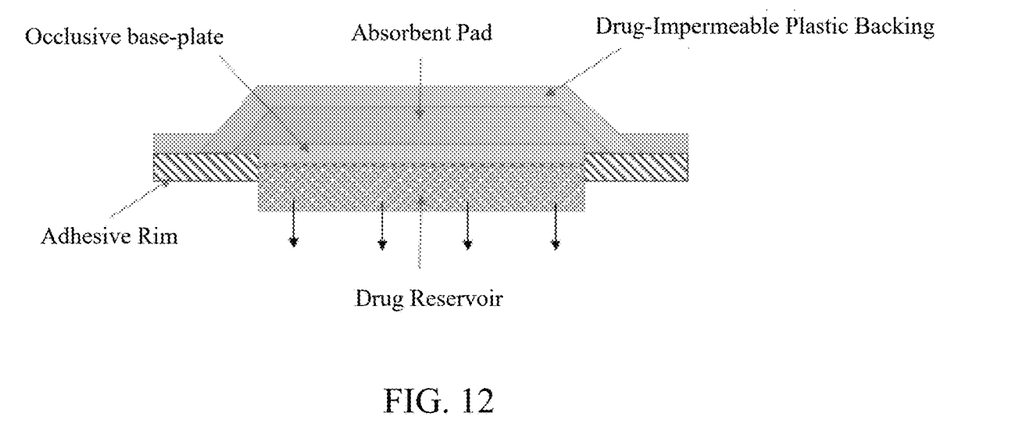
FIG. 12 is an illustration showing a cross-sectional view of an exemplary matrix diffusion controlled transdermal drug delivery system.

Matrix Diffusion-Controlled System: In this approach for a transdermal drug delivery system, the drug reservoir is prepared by homogenously dispersing drug particles in a hydrophilic or lipophilic polymer matrix. The resultant medicated polymer is then molded into a medicated disc with a defined surface area and controlled thickness. This drug reservoir containing polymer disc is then pasted on to an occlusive base plate in a compartment fabricated from a drug impermeable plastic backing. The adhesive polymer is then spread along the circumference to form a strip of adhesive rim around the medicated disc.[8] An example of a matrix diffusion-controlled system is illustrated within FIG. 12 which shows a cross-section view of a matrix diffusion controlled transdermal delivery system showing major structural components.

In addition to palmar-plantar erythrodysesthesia, the medicinal composition disclosed herein may be used to treat any number of other skin related conditions, including but not limited to poison ivy, diaper rash, eczema, and various types of burns including but not limited to thermal burns, electrical burns, radiation burns and sun burns. The medicinal composition may also be used to treat certain neuropathic conditions (e.g., diabetic neuropathy) where patient's feel a tingling sensation in their hands and feet.

Numerous embodiments have been described herein. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof. The phrase "associated with" as used in this document, refers to structures which support the disclosed device and may also refer to structures not disclosed herein capable of supporting the disclosed device. Further, the "invention" as that term is used in this document is what is claimed in the claims of this document. The right to claim elements and/or sub-combinations that are disclosed herein as other inventions in other patent documents is hereby unconditionally reserved.

REFERENCES 1. (Kapadia, G. J.; Fayez, M. B. E.; Sethi, M. L., 1969: Hennosides, the primary glycosidic constituents of Henna. Lloydia, 32: 523).
2. http://www.yourarticlelibrary.com/pharmacognosy/photochemical-screening/glycoside-in-plant-isolation-and-types-of-glycoside-in-plant/49417
3. https://www.researchgate.net/post/What_is_the_best_method_to_extract_lawsone_from_Henna)
4. Method 2: Sum of HFS-affected patients by cancer type, chemotherapy type (Excel File; Market Research compiled by BioEnterprise, an independent third-party)

5. https://www.drugs.com/pro/doxorubicin-liposomal.html
6. Invest New Drugs. 2008 April; 26(2): 189-92. Epub 2007 Sep. 21. Topical Henna for capecitabine induced hand-foot syndrome. Yucel I(1), Guzin G.
7. https://www.breastcancer.org/treatment/side_effects/hand_foot_synd
8. https://www.pharmatutor.org/articles/detail-information-on-transdermal-patches
9. Hsouna, A. B., Trigui, M., Culioli, G., Blache, Y., Jaoua, S., "Antioxidant constituents from *Lawsonia inermis* leaves: Isolation, structure elucidation and antioxidative capacity", Food Chemistry, 6, 2010, pp. 176-183.
10. https://www.ecfr.gov/cgibin/retrieveECFR?gp=&SID=a95399fff2ebb35afcbbbe4e4cf897c6&r=PART&n=21y1.0.1.1.27#se21.1.73_12190

Having thus described the disclosed method and apparatus, it is now claimed:

1. A method of making a topical treatment medicinal composition comprising:
    providing 2-hydroxy-1,4, naphthoquinone;
    combining 2-hydroxy-1,4, naphthoquinone with a glycoside to activate analgesic properties within the 2-hydroxy-1,4, naphthoquinone and form a concentrated suspension.

2. The method of making the topical treatment medicinal composition according to claim 1, wherein the 2-hydroxy-1,4, naphthoquinone is synthetically manufactured or is obtained from a natural source.

3. The method of making the topical treatment medicinal composition according to claim 2, wherein the glycoside is synthetically manufactured or is obtained from a natural source and comprises an aglycone bound to a glycone.

4. The method of making the topical treatment medicinal composition according to claim 3, wherein the glycone is an alpha hydroxyl acid.

5. The method of making the topical treatment medicinal composition according to claim 4, wherein the alpha hydroxyl acid is one of the following: malic acid, citric acid, tartaric acid and mandelic acid.

6. The method of making the topical treatment medicinal composition according to claim 5, wherein the glycoside is any one of the following: Anthraquinones glycosides, Cardiac glycosides, Saponin glycosides, Tetracyclic Triterpenoids saponins, Pentacyclic Triterpenoid saponins, Coumarin and furocoumarin glycosides, Cyanophore glycosides, Flavonoids glycosides, Flavone glycosides, Flavonol glycosides, FlacanOne glycosides, Chalone glycosides, Isoflavonoid glycoside, Anthocyanidin glycosides, Isothiocyanate glycosides, Phenol glycoside, Aldehyde glycosides, Bitter glycosides and combinations thereof.

7. The method of making the topical treatment medicinal composition according to claim 6, wherein the concentrated suspension of 2-hydroxy-1,4, naphthoquinone and glycoside is combined with inactive and/or active ingredients.

8. The method of making the topical treatment medicinal composition according to claim 6, wherein the concentrated suspension is combined with a compound selected from the group consisting of: a topical steroid, a topical nonsteroidal anti-inflammatory drug, an antiarrhythmic, aloe vera, a topical emollient, a carrier oil, an essential oil, an essential oil selected from the group consisting of tea tree oil, *eucalyptus* oil, frankincense, lavender and combinations thereof.

9. The method of making the topical treatment medicinal composition according to claim 1, wherein the 2-hydroxy-1,4, naphthoquinone is extracted from a Henna plant.

10. The method of making the topical treatment medicinal composition according to claim 9, wherein the glycoside is obtained from lemon juice.

11. The method of making the topical treatment medicinal composition according to claim 10, comprising the following steps:
    adding ⅔ of a cup of aloe juice to a pot;
    heating the pot to bring the aloe juice to a boil;
    reducing the heat to allow the aloe juice to simmer;
    adding one-half cup or from about 30 to about 50 grams of Henna to the aloe juice;
    mixing the Henna and aloe juice;
    adding from about 0.16 to about 0.6 fluid ounces of lemon juice, from about 0.16 to about 0.6 fluid ounces of coconut oil and from about 0.4 to about 0.6 fluid ounces of each of tea tree oil, *eucalyptus* oil and frankincense;
    removing the pot from the heat and mixing its contents;
    adding water as necessary to obtain the desired consistency to form a liquid, paste or cream; and
    storing the liquid, paste or cream in a container in a refrigerator.

* * * * *